United States Patent [19]

Shimamoto et al.

[11] Patent Number: 5,431,652

[45] Date of Patent: Jul. 11, 1995

[54] BONE-TREATING DEVICES AND THEIR MANUFACTURING METHOD

[75] Inventors: Takeshi Shimamoto, Fukuchiyama; Takashige Oka, Funai; Minori Adachi, Ayabe; Suon H. Hyon, Uji; Kazuo Nakayama, Ushiku; Akira Kaito, Ibaragi, all of Japan

[73] Assignees: Gunze Limited, Ayabe; Agency of Industrial Science and Technology, Tokyo, both of Japan

[21] Appl. No.: 994,788

[22] Filed: Dec. 22, 1992

[30] Foreign Application Priority Data

Dec. 25, 1991 [JP] Japan .................. 3-357752

[51] Int. Cl.6 .................................................. A61B 17/56
[52] U.S. Cl. ................................................ 606/76; 606/77
[58] Field of Search ............................. 606/72–77; 623/13, 16, 11, 66; 525/410, 415; 528/354

[56] References Cited

U.S. PATENT DOCUMENTS

| | | |
|---|---|---|
| 3,636,956 | 1/1972 | Schneider . |
| 4,539,981 | 9/1985 | Tunc ............................ 606/77 |
| 4,550,449 | 11/1985 | Tunc . |
| 4,781,183 | 11/1988 | Casey ........................... 606/77 |
| 4,898,186 | 2/1990 | Ikada ............................ 606/77 |
| 4,968,317 | 11/1990 | Törmälä ....................... 606/77 |
| 5,007,939 | 4/1991 | Delcommune ................ 606/77 |
| 5,037,950 | 8/1991 | Bezwada ...................... 606/77 |

FOREIGN PATENT DOCUMENTS

| | | |
|---|---|---|
| 52-13230 | 4/1977 | Japan . |
| 3-29663 | 2/1991 | Japan . |
| 3-103429 | 4/1991 | Japan . |

OTHER PUBLICATIONS

B. Eling et al., *Polymer*, vol. 23, No. 11, pp. 1587–1593 (1982).
K. Nakamura et al., *Kobunshi Ronbunshu*, vol. 43, No. 1, pp. 25–30 (1986); (English abstract included).

*Primary Examiner*—Michael A. Brown
*Attorney, Agent, or Firm*—Armstrong, Westerman, Hattori, McLeland & Naughton

[57] ABSTRACT

Bone-treating devices made of biodegradable polymers having a high-density and a high-orientation along the major axis, which have a density of 1.260 g/cm³ or more (when measured by the sink and float method) and which possess the bending strength and the bending strength-retaining characteristic defined by the following equations:

$$A \geqq B \geqq 23 \ (kgf/mm^2) \quad (1)$$

$$B/A \geqq 0.85 \quad (2)$$

wherein A is the initial bending strength and B is the bending strength after 90-days immersion of the devices in a phosphate buffer at 37° C. and preparing the same.

17 Claims, 2 Drawing Sheets

BONE-TREATING DEVICES AND THEIR MANUFACTURING METHOD

FIELD OF THE INVENTION

The invention pertains to devices which are to be used for fusing and fixing the fractured bones, fixing the bone grafts, and for fixing the periarticular fractured areas. The invention particularly pertains to devices made of biodegradable polymers.

BACKGROUND OF THE INVENTION

Devices which have been conventionally used for bone treatment include wires, plates, screws, pins, staples, clips, rods, etc., which are made of stainless steel, ceramic, etc. The bending strength of these conventional devices is adequately high (about 33 kgf/mm$^2$ for devices made of SUS-316 stainless steel and about 25-50 kgf/mm$^2$ for devices made of ceramics). However, they are not biodegradable and hence require a re-operation for their removal after healing. Furthermore, since they are more rigid than human bones, the use of these devices in vivo can cause problems such as bone shaving, local osteolysis due to continuous stimulation, a reduction in the strength of newly formed bones, and delay in the growth of regenerated bones.

Until now, several bone-treating devices made of biodegradable polymers have been proposed. However, these devices are inferior to the devices made of stainless steel, ceramic, etc. in terms of the bending strength and the stiffness to endure torsion, bending, etc. Furthermore, these biodegradable devices retain a therapeutically necessary strength only for less than 3 months (often about 1-2 months). It is therapeutically ideal that biodegradable bone-treating devices retain a therapeutically necessary strength for about 3 months and subsequently lose their strength rapidly by means of their decomposition in vivo, eventually leading to bioabsorption.

To improve the shortcomings of conventional biodegradable bone-treating devices, the applicants previously proposed an invention (Japanese Examined Patent Publication No. 1991-63901). That invention pertained to improving the initial strength and the strength-retaining characteristic by means of drawing and stretching molded biodegradable lactic acid polymers along their major axis in air or fluid under heating condition. The same proposal has also been made in the Japanese Unexamined Patent Publication No. 1991-29663.

However, the above-mentioned technique can not adequately improve the strength. It was difficult or impossible with that technique to manufacture bone-fusing devices whose initial strength is comparable to that of devices made of stainless steel or ceramic. As shown in the comparative examples 1-2, to be stated later, the density and the bending strength of an cylindrical product, manufactured by melting and extruding poly-L-lactic acid (about 400,000 in viscosity-average molecular weight), was 1,250 g/cm$^3$ and 22.0 kgf/mm$^2$, respectively, when the drawing was performed at a ratio of 4:1 in an oil bath at 140° C. They were 1.250 g/cm$^3$ and 22.6 kgf/mm$^2$ when the draw ratio was 9.8:1. These values indicate a limit of that technique. The unsatisfactory results may be attributable to the enlargement of the slight voids (which had been produced during molding) due to the drawing procedure at elevated temperatures after molding at normal pressure. This explanation is supported by the finding that increase of drawing ratio causes no increase in the density based on the molecular arrangement. None of the previously proposed bone-treating devices, made of biodegradable polymers, had a density and bending strength higher than the above-mentioned levels.

The present invention is purposed to resolve the above-mentioned problems, i.e., to provide those bone-treating devices made of biodegradable polymers which have an initial strength comparable to that of similar devices made of stainless steel or ceramic; which retain a therapeutically necessary strength for adequate periods; and which rapidly lose their strength by means of hydrolysis and are eventually absorbed in vivo after elapse of the therapeutically necessary periods.

SUMMARY OF THE INVENTION

The present invention pertains to high-density bone-treating devices in which biodegradable polymer molecules are oriented along the major axis. Their density is 1.260 g/cm$^3$ or more when examined by the sink and float method. Furthermore, these devices possess the bending strength and the bending strength-retaining characteristic defined by the following equations:

$$A \geq B \geq 23 \text{ (kgf/mm}^2\text{)} \tag{1}$$

$$B/A \geq 0.85 \tag{2}$$

wherein A is the initial bending strength and B is the bending strength after 90-days immersion of the devices of the invention in a phosphate buffer at 37° C.

DETAILED DESCRIPTION OF THE INVENTION

In this statement, the density indicates the reading by the sink and float method (pycnometer) at 23° C., using a carbon tetrachloride-heptane mixture. The initial strength (A) is the bending strength of a test material before immersion, measured according to the JIS K7203. The bending strength after immersion (B) is measured in the same way as above after 90-days immersion of the test material in a phosphate buffer (containing 0.9% NaCl) at 37° C.

Figure 4:
FIG. 4 demonstrates a microscope picture presenting the crystal structure of the bone-treating device (obtained in Example 2)

The bone-treating devices of the invention are also improved in other mechanical properties, such as tensile strength, compression strength, impact force, hardness degree, shear force, tensile fatigue resistance, bending fatigue resistance, compression fatigue resistance, etc. due to orientation effect of biodegradable polymer molecules exerted by hydrostatic extrusion in comparison with the devices prepared by conventional drawing method. Improvement of properties of fatigue resistances (tensile, bending and compression) has an excellent effect on resistance to repeated loading while walking and to thoracic movement when breathing. In particular, the bone-treating devices prepared by the method of the invention keep an original shape (like a bamboo) without being broken and reparated unlike the conventional bone-treating devices obtained by press molding or injection molding, even when a loading more than the maximum load is applied to the device of the invention. FIG. 4 shows orientation of biodegradable polymer of the present invention. The above-mentioned features decrease postoperative disorders such as osteosynthesis failure caused by transaction of a bone-treating device to a substantial extent.

As shown above, the invention exerts a great effect on a special field as bone-treatment.

The bending strength of the thus manufactured bone-treating devices is much higher than that of human cortical bone (20 kgf/mm² or less) and is comparable to that of devices made of stainless steel or ceramic. Furthermore, these devices of the invention have a high density and a stiffness against torsion or bending stress. They retain a therapeutically necessary strength for 3 months, a period necessary for treatment. Subsequently, the devices rapidly lose their strength due to hydrolysis in vivo. Thus, the devices have features ideal as bone-treating devices.

When the cross-section of these devices was observed by microscopy photographs and X-ray diffraction, the devices consisted of biodegradable polymer molecules were found to be characterized by their high-density and high-orientation along the major axis. The density was as high as 1.260 g/cm³ or more, a density which has not been reported for any conventional bone-treating device made of biodegradable polymers. Such a high density indicates that the products are free of crystal voids in their inside and of cracks, etc. The desirable density range is 1,265-1.285 g/cm³. The initial bending strength of these bone-treating devices was as high as 23 kgf/mm² or more. In some instances, the initial bending strength was about 40 kgf/mm². These levels of the bending strength are comparable to those known for devices made of stainless steel or ceramic. Such a high bending strength has not been reported for any device made of biodegradable polymers. The desirable range of the initial bending strength is 25-38 kgf/mm². Another characteristic of the thus-manufactured bone-treating devices lies in their excellent capacity of retaining strength. After 90-days immersion of the devices in phosphate buffer at 37° C. the bending strength was 90% or more of the initial bending strength and was 23 kgf/mm² or more. This indicates that these devices do not show a sharp decrease in their strength, caused by hydrolysis, for 90 days in vivo. Therefore, these devices preserve the strength necessary for treatment for about 3 months (a period necessary for bone treatment). After elapse of about 3 months, the devices rapidly lose their strength and are absorbed in vivo. Therefore, these devices require no re-operation for their removal. The desirable characteristic of strength preservation can be defined by the above-mentioned equations (1') and (2') as follows:

$$A \geq B \geq 25 \ (kgf/mm^2) \quad (1')$$

$$B/A \geq 0.90 \quad (2')$$

The biodegradable polymers of the invention encompass various polymers which can be hydrolyzed and absorbed in vivo. For example, they include poly-L-lactic acid; poly-D-lactic acid; poly-D,L-lactic acid; copolymer of L-lactic acid and D-lactic acid; copolymer of L-lactic acid and D,L-lactic acid; copolymer of D-lactic acid and D,L-lactic acid; a stereo complex produced by mixing poly-L-lactic acid and poly-D-lactic acid; polyglycolic acid; copolymer of L-lactic acid and glycolic acid; copolymer of D-lactic acid and glycolic acid; copolymer of D,L-lactic acid and glycolic acid, etc. These polymers can also be used in blends. Of these polymers, the polymers primarily made of lactic acid (i.e., lactic acid polymers) or their copolymers are particularly favorable. The strength and preservation thereof are particularly excellent with polymers primarily composed of L-lactic acid such as: poly-L-lactic acid; copolymers primarily made of L-lactic acid (e.g., copolymers of L-lactic acid and D-lactic acid, copolymers of L-lactic acid and D,L-lactic acid); and stereo complex produced by mixing poly-L-lactic acid and poly-D-lactic acid.

The molecular weights of the above-mentioned biodegradable polymers vary widely. Their molecular weights tend to be reduced by their own degradation by heat. Therefore, if we consider a reduction in molecular weights during manufacturing processes, it is desirable to use polymers with a viscosity-average molecular weight of 50,000 or more as a raw material. Considering the features such as degradation, strength preservation, processability and cost, the optimum viscosity-average molecular weights are about 250,000 to about 500,000.

Articles for bone-treating devices are manufactured by melting and extruding the above-mentioned biodegradable polymers by the routine method and subsequently processing the polymers into a desired shape, using extrusion or any other appropriate method. The articles are also prepared by heat-treatment at 120°±20° C. in an oil bath or under vacuum. The articles are also prepared by melting biodegradable polymer at 200°±20° C. under high pressure (not less than 50 MPa), followed by crystallization under High pressure. The thus obtained articles are then subjected to hydrostatic extrusion.

The hydrostatic extrusion itself is a technique that has been used for polymers such as polyethylene, polypropylene, Nylon 12 and polyacetal (see, for example, Japanese Examined Patent Publication No.1977-13230). However, to our knowledge, there is no published report of applying hydrostatic extrusion to biodegradable polymers. Furthermore, no report has been published regarding the features of thus-obtained products and their strength preservation in vivo. The present invention has revealed for the first time that bone-treating devices with ideal features can be produced by applying hydrostatic extrusion to biodegradable polymers. Hydrostatic extrusion is performed, for example, using the system shown in FIG. 1, which is composed of an extruding container (1), a die (2) and an extruding ram (3). The space (5) between the polymer (4) and the extruding container (1) is filled with a pressure medium (glycerin, for example). While heating, a pressure is applied to the ram (3) in the P direction to indirectly extrude the polymer.

Figure 2:
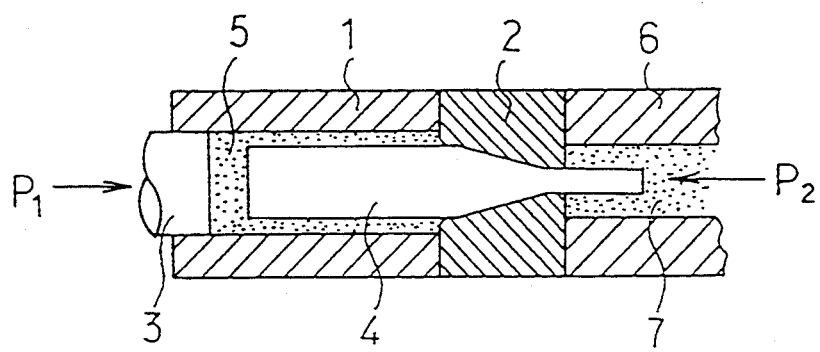
FIG. 2 demonstrates a cross-sectional view presenting some other aspects of the hydrostatic extruder used with the present invention.
Figure 3:
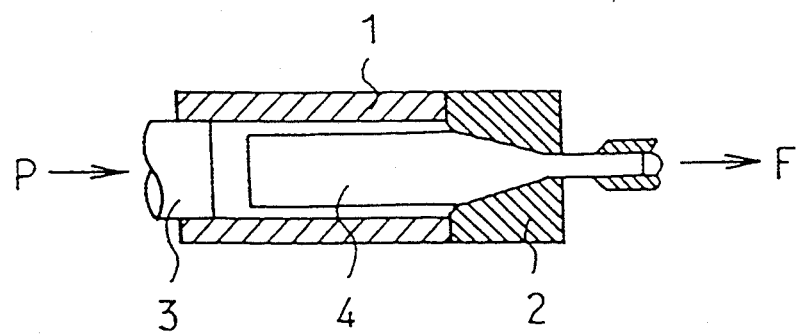
FIG. 3 demonstrates a cross-sectional view presenting the other aspects of the hydrostatic extruder used with the present invention.

With the method shown in FIG. 2, the space (7) in the receiving container (6) is filled with a pressure medium. This method, which is called differential pressure extrusion, is expected to exert a more high-pressure effect by applying a smaller pressure (P2) than the extruding pressure (P1) to the ram in the opposite direction. As shown in FIG. 3, it is also possible to extrude by means of drawing the material in the F direction, thus allowing the extruded material to remain straight, and its surface good.

If the above-mentioned hydrostatic extrusion is applied to biodegradable polymers, it is possible to apply a uniform and high pressure to the entire polymers while suppressing the, heat-caused decrease in their molecular weights (a feature of this type of polymers). The thus-formed bone-treating devices have few voids, high density and excellent strength. In addition, their hydrolysis rate in vivo is controlled appropriately, and they have the capacity of preserving the strength as defined by the above-mentioned equations (1) and (2). Bone-treating devices made of biodegradable polymers, which have such features, cannot be produced by drawing, die stretching or ram extrusion techniques.

It is desirable that hydrostatic extrusion be done between the polymer's glass transition point and the melting point. It is particularly desirable that it be performed at temperatures slightly lower than the melting point, i.e., at about 90° to about 170° C. in the case of poly-L-lactic acid, about 120° to about 220° C. in the case of polyglycolic acid, and about 90° to about 230° C. in the case of copolymers. The desirable extrusion ratio is 4:1 to 15:1. If the extrusion ratio is high, the density of the polymers is increased, leading to a higher capacity of strength preservation in vivo. With conventional extrusion or drawing techniques, voids and cracks are likely to develop at high extrusion ratios, leading to a substantial decrease in the strength and the strength-retaining capacity. Such problems do not arise with the technique of the invention even at high extrusion ratios. The optimum temperature and ratio of extrusion for poly-L-lactic acid are 140°±10° C. and 5:1 to 10:1, respectively.

In performing this technique, it is most desirable that extrusion is done twice or more to achieve a desired extrusion ratio and a desired quality. For example, it is recommended that extrusion be done twice (first at 90° C. with an extrusion ratio of 2:1 and then at 170° C. with an extrusion ratio of 2:1) to achieve a 4:1 extrusion ratio. Such a method allows extrusion at relatively low temperatures, thus minimizing the heat-induced decrease in the molecular weight and allowing gradual arrangement of the molecular chains. In this way, products with higher quality, compared to products obtained by a single extrusion at the same ratio, can be obtained.

The product obtained by hydrostatic extrusion is heat-treated at 120°±20° C. for a long time (at least 12 hours) in an oil bath or under vacuum while fixing both ends of the product or inserting the product into a metal pipe to maintain the shape of the extruded product. The heat-treatment can be performed under high-pressure (at least 50 MPa). The post-extrusion treatment improves degree of crystallinity and orientation of the bone-treating devices.

The extrusion ratio with this technique is expressed using the cross-sectional area (in the direction of extrusion) of the polymer (4) which fills the extruding container (1) and the inner cross-sectional area (in the same direction) of the die (2). If the cross-sectional area of the polymer (4) is 1 and the cross-sectional area of the die (2) is ⅓, the extrusion ratio is 3:1.

The bone-treating devices manufactured by the hydrostatic extrusion of the invention can have various shapes necessary for fixing bones. Possible shapes include, for example, wires, plates, screws, pins, plugs, wedges, arrowheads, pegs, staples, clips, rods, spacers, nuts, hooks, washers, caps, buttons, fillers, etc. Since the technique of the invention increases the strength of materials per unit area, it is possible to manufacture devices with a small width and size. It is also possible with this technique to manufacture products which are highly transparent.

EXAMPLE

To characterize the present invention, some examples of the invention will be presented.

Examples 1 and 2

Powdered poly-L-lactic acid (viscosity-average molecular weight: 400,000) was made into pellets with a pelletizer. Subsequently, the pellets were melted, mixed and extruded at 200° C. to yield cylindrical products of various diameters.

Figure 1:
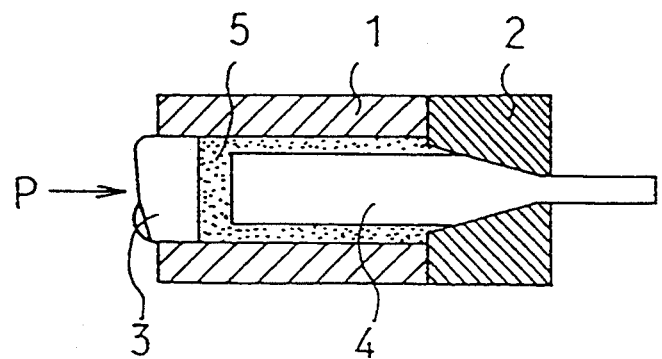
FIG. 1 demonstrates a cross-sectional view of the hydrostatic extruder used with the present invention.

These products were subjected to hydrostatic extrusion at 140° C. and an extrusion rate of 5.0 mm/min, using a glycerin-filled extruder (die diameter=5 mm, shown in FIG. 1). The extrusion ratios are shown in Table 1. At an extrusion ratio of 4:1 (Example 1), the diameter of the cylindrical product was 10.0 mm. At an extrusion ratio of 8:1 (Example 2), the diameter was 14.14 mm.

The physical properties of the products of extrusion are shown in Table 1. The density, initial bending strength and the bending strength after 90-days immersion were measured according to the methods mentioned above. The viscosity-average molecular weight was calculated according to the following equation using intrinsic viscosity $\eta$:

$$[\eta] = 5.45 \times 10^{-4} M_v^{0.73}$$

where $\eta$ was measured in chloroform at 25° C., and Mv is the viscometric average molecular weight.

FIG. 4 shows a microscope picture of the cross-section of the extrusion product (Example 2). The picture shows that thin layers, formed by fibrillation of polymer molecules arranged along the major axis, densely overlap each other.

TABLE 1

(Examples 1 and 2)

| Example No. | Extrusion ratio | Density (g/cm³) | Viscosity average molecular weight (× 10,000) | Initial bending strength (kgf/mm²) | Bending Strength after 90-days immersion (kfg/mm²) |
| --- | --- | --- | --- | --- | --- |
| Reference sample | 1 | 1.2497 | 18.1 | 12.5 | 5.3 |
| 1 | 4 | 1.2601 | 18.3 | 27.2 | 24.5 |
| 2 | 8 | 1.2705 | 16.0 | 34.4 | 33.0 |

Comparative Examples 1 and 2

The cylindrical product (Example 1) was subjected to monoaxial drawing along the major axis in an oil bath (140° C.). The drawing ratio and the characteristics are shown in Table 2.

TABLE 2
(Reference examples 1 and 2)

| Reference Example No. | Drawing ratio | Density (g/cm³) | Viscosity average molecular weight (× 10,000) | Initial bending strength (kgf/mm²) | Bending Strength after 90-days immersion (kfg/mm²) |
|---|---|---|---|---|---|
| Reference sample | 1 | 1.2497 | 18.1 | 12.5 | 5.3 |
| 1 | 4 | 1.2499 | 17.6 | 22.0 | 13.6 |
| 2 | 9.8 | 1.2500 | 18.3 | 22.6 | 16.9 |

Tables 1 and 2 include the following suggestions. As shown in Table 2, the magnitude of increase in the density was minimal with the conventional drawing method. That is, the density cannot be elevated over 1.2500 g/cm³ with the conventional technique even at a draw ratio of 9.8:1. Although the initial bending strength can also be elevated by drawing, the difference in the strength is very small between a 4:1 drawing and a 9.8:1 drawing. Thus, the drawing technique cannot increase the bending strength over about 22 kgf/mm². The products manufactured by drawing showed a marked decrease in their strength after 90-days immersion. Thus, these products did not retain an therapeutically adequate strength for a therapeutically necessary period.

The bone-treating pins, manufactured by the technique of the invention, had a high density (1,260 g/cm³). Their bending strength was as high as 27.2 kgf/mm² at an extrusion ratio of 4:1. When the extrusion ratio was increased to 8:1, the bending strength also rose to 34.4 kgf/mm². After 90-days immersion the strength decreased only slightly, retaining 85% or more (90% or more in some cases) of the initial strength. The strength after 90-days immersion was 23 kgf/mm² or more. These results indicate that the pins manufactured by the present invention can retain a therapeutically adequate strength for a therapeutically necessary period in vivo.

Examples 3 to 8

As in Example 1, cylindrical products were manufactured and subjected to hydrostatic extrusion. The extrusion conditions and the characteristics of the products are shown in Table 3. At an extrusion ratio of 10:1, a cylindrical product with a diameter of 15.81 mm was used.

TABLE 3

| Example No. | Extruding conditions Temperature (°C.) | Ratio | weight (t) | Density (g/cm³) | Viscosity average molecular weight (× 10,000) | Initial bending strength (kgf/mm²) | Bending Strength after 90-days immersion (kgf/mm²) |
|---|---|---|---|---|---|---|---|
| 3 | 90 | 4 | 8.8 | 1.2609 | 23.2 | 27.9 | 25.1 |
| 4 | 95 | 4 | 10.0 | 1.2612 | 22.1 | 27.7 | 25.2 |
| 5 | 110 | 4 | 5.3 | 1.2607 | 20.4 | 27.5 | 24.6 |
| 6 | 130 | 4 | 4.4 | 1.2601 | 18.0 | 26.2 | 23.7 |
| 7 | 130 | 8 | 5.9 | 1.2710 | 16.8 | 32.1 | 30.2 |
| 8 | 140 | 10 | 4.0 | 1.2762 | 18.4 | 33.6 | 32.2 |

Examples 9 to 11

As in Example 1, cylindrical products, manufactured by melting and molding, were subjected to two cycles of hydrostatic extrusion at the conditions shown in Table 4. The characteristics of the products are shown in Table 5.

TABLE 4

| Example No. | First extruding conditions Temperature (°C.) | Ratio | Second extruding conditions Temperature (°C.) | Ratio |
|---|---|---|---|---|
| 9 | 120 | 4 | 140 | 1.5 |
| 10 | 120 | 4 | 140 | 2 |

TABLE 5

| Example No. | Density (g/cm³) | Viscosity average molecular weight (× 10,000) | Initial bending strength (kgf/mm²) | Bending Strength after 90-days immersion (kgf/mm²) |
|---|---|---|---|---|
| 9 | 1.2651 | 16.9 | 28.8 | 26.8 |
| 10 | 1.2710 | 17.2 | 33.5 | 32.2 |

Table 5 indicates that the products obtained by multiple cycles of hydrostatic extrusion have a higher strength than the products obtained by a single hydrostatic extrusion at the same extrusion ratio.

I. Experiment in Vitro

The bar-shaped extrusion product (Example 2) was processed by cutting and attaching a taper to both ends, to yield a rib-fixing pin. This fixing pin was immersed in phosphate-buffered saline (PBS), which contained 0.9 w/w % NaCl, at 37° C., for the purpose of examining the time course of hydrolysis. As shown in Table 6, the pin retained a high strength even after 90-days immersion. From the 90th day on, the pin rapidly decreased its strength.

TABLE 6

| Days of immersion | 0 | 56 | 70 | 90 | 105 | 126 | 180 | 240 | 300 |
|---|---|---|---|---|---|---|---|---|---|
| Bending strength (kgf/mm²) | 34.4 | 34.4 | 34.1 | 33.0 | 24.1 | 17.2 | 12.1 | 6.7 | 3.2 |
| Percentage of strength retained (%) | 100 | 100 | 99 | 96 | 70 | 50 | 35 | 19 | 9 |

The bending strength decreased to 50% of the initial strength on 126th day and to 9% on 300th day.

II. Experiment in Animals

Five adult mongrel dogs, weighing 10 kg on average, underwent local incision under intramuscular anesthesia. The 9th, 10th and 11th ribs on the left side were removed together with the periosteum at the level about 2-4 cm apart from the costal edge. The above-mentioned pin was inserted into the costal bone marrow to fuse the dissected region. This region was then ligated with silk threads to fix the joint region. In one of these dogs, the operated area was observed on X-ray films every week. This observation revealed successful bone fusion one month later. In the other dogs, the operated area was resected en block 2 weeks, 1, 2 or 3 months later for observation of tissue reaction of the ribs, the external appearance of the pin, and changes in the physical properties of the pin.

These observations revealed no noteworthy problem. The change in the pin's physical properties was similar to that observed in vitro.

We claim:

1. Bone-treating devices made of biodegradable polymers having a high-density and a high-orientation along the major axis, which have a density of 1,260 g/cm³ or more (when measured by the sink and float method) and which possess the bending strength and the bending strength-retaining characteristic defined by the following equations:

$$A \geq B \geq 23 \text{ (kgf/mm}^2) \tag{1}$$

$$B/A \geq 0.85 \tag{2}$$

wherein A is the initial bending strength and B is the bending strength after 90-days immersion of the devices in a phosphate buffer at 37° C.

2. Bone-treating devices as defined in claim 1, which have a density between 1.265 and 1,285 g/cm³.

3. Bone-treating devices as define in claim 1, which have the bending strength and the bending strength-retaining characteristic expressed by the following equations:

$$A \geq B \geq 25 \text{ (kgf/mm}^2) \tag{1'}$$

$$B/A \geq 0.90 \tag{2'}$$

wherein A is the initial bending strength and B is the bending strength after 90-days immersion of the devices in a phosphate buffer at 37° C.

4. The devices as defined in claim 1, in which lactic acid polymers with a viscosity-average molecular weight of 50,000 or more as a raw material are used as biodegradable polymers.

5. The devices as defined in claims 4, in which L-lactic acid polymers are used as lactic acid polymers.

6. The devices as defined in claim 4, in which lactic acid polymers have a viscosity-average molecular weight of 250,000 to 500,000.

7. The method for manufacturing bone-treating devices comprising hydrostatically extruding biodegradable polymers by applying pressure to a pressure medium so as to indirectly extrude the biodegradable polymer at a temperature between the glass transition point and the melting point thereof to produce high-density products in which the molecules of the polymer are oriented along the major axis and which have a density of 1,260 g/cm³ or more when measured by the sink and float method, and the bending strength and the bending strength-retaining characteristic defined by the following equations:

$$A \geq B \geq 23 \text{ (kgf/mm}^2) \tag{1}$$

$$B/A \geq 0.85 \tag{2}$$

where A is the initial bending strength and B is the bending strength after 90-days immersion of the devices in a phosphate buffer at 37° C.

8. The method as defined in claim 7, wherein the polymer is extruded at an extrusion rate of 4:1 to 15:1.

9. The method as defined in claim 8, wherein the polymer is extruded at least 2 times to yield a total extrusion ratio of 4:1 to 15:1.

10. The method as defined in claim 7, in which lactic acid polymers are used as biodegradable polymers.

11. The method as defined in claims 10, in which L-lactic acid polymers are used as lactic acid polymers.

12. The method as defined in claim 10, in which the temperature and ratio of extrusion for poly-L-lactic acid are 140°±10° C. and 5:1 to 10:1, respectively.

13. The method as defined in claim 7 wherein the devices have the bending strength and the bending strength-retaining characteristic expressed by the following equations:

$$A \geq B \geq 25 \text{ (kgf/mm}^2) \tag{1'}$$

$$B/A \geq 0.90 \tag{2'}$$

wherein A is the initial bending strength and B is the bending strength after 90-days immersion of the devices in the phosphate buffer at 37° C.

14. The method as defined in claim 7, wherein the polymer is extruded at a temperature between the glass transition point and the melting point of the polymer.

15. The method as defined in claim 14, wherein the polymer is extruded at a temperature slightly lower than the melting point of the polymer.

16. A method for manufacturing bone-treating devices comprising differential pressure extrusion of biodegradable polymers by hydrostatically applying first pressure ($P_1$) in a direction of extrusion and second counter pressure ($P_2$), in which $P_1$ is larger than $P_2$, at a temperature between the glass transition point and the melting point thereof to produce high-density products in which the molecules of the polymer are oriented along the major axis and which have a density of 1,260 g/cm³ or more when measured by the sink and float method, and the bending strength and the bending strength-retaining characteristic defined by the following equations:

$$A \geq B \geq 23 \text{ (kgf/mm}^2) \tag{1}$$

$$B/A \geq 0.85 \tag{2}$$

where A is the initial bending strength and B is the bending strength after 90-days immersion of the devices in a phosphate buffer at 37° C.

17. A method for manufacturing bone-treating devices comprising extruding biodegradable polymers by applying hydrostatical pressure (P) and drawing pressure (F), in which P and F are applied in a direction of extrusion at a temperature between the glass transition point and the melting point thereof to produce high-density products in which the molecules of the polymer are oriented along the major axis and which have a density of 1,260 g/cm³ or more when measured by the sink and float method, and the bending strength and the bending strength-retaining characteristic defined by the following equations:

$$A \geqq B \geqq 23 \text{ (kgf/mm}^2\text{)} \tag{1}$$

$$B/A \geqq 0.85 \tag{2}$$

where A is the initial bending strength and B is the bending strength after 90-days immersion of the devices in a phosphate buffer at 37° C.

* * * * *